(12) United States Patent
Khandkar et al.

(10) Patent No.: US 6,589,239 B2
(45) Date of Patent: Jul. 8, 2003

(54) ELECTROSURGICAL KNIFE

(76) Inventors: Ashok C. Khandkar, 2116 Lakeline Dr., Salt Lake City, UT (US) 84109; Aaron A. Hofmann, 5926 Brentwood Dr., Salt Lake City, UT (US) 84121-1506

( * ) Notice: Subject to any disclaimer, the term of this patent is extended or adjusted under 35 U.S.C. 154(b) by 13 days.

(21) Appl. No.: 10/020,860

(22) Filed: Dec. 13, 2001

(65) Prior Publication Data

US 2002/0111622 A1 Aug. 15, 2002

Related U.S. Application Data

(63) Continuation-in-part of application No. 09/495,570, filed on Feb. 1, 2000, now Pat. No. 6,409,725.

(51) Int. Cl.[7] ............................................. A61B 18/18
(52) U.S. Cl. ........................................ 606/45; 606/29
(58) Field of Search ............................ 606/41, 45–52, 606/27–29

(56) References Cited

U.S. PATENT DOCUMENTS

| | | |
|---|---|---|
| 3,913,583 A | 10/1975 | Bross |
| 4,033,351 A | 7/1977 | Hetzel |
| 4,161,950 A | 7/1979 | Doss et al. |
| 4,232,676 A | 11/1980 | Herczog |
| 4,248,231 A | 2/1981 | Herczog et al. |
| 4,314,559 A | 2/1982 | Allen |
| 4,333,467 A | 6/1982 | Domicone |
| 4,481,057 A | 11/1984 | Beard |
| 4,785,807 A | 11/1988 | Blanch |
| 4,848,337 A * | 7/1989 | Shaw et al. |
| 4,876,110 A | 10/1989 | Blanch |
| 5,197,962 A * | 3/1993 | Sansom et al. |
| 5,925,039 A * | 7/1999 | Landingham |
| 5,925,043 A * | 7/1999 | Kumar et al. |
| 6,270,831 B2 * | 8/2001 | Kumar et al. ............... 427/2.24 |
| 6,468,642 B1 * | 10/2002 | Bray et al. ................... 428/216 |

OTHER PUBLICATIONS

"Porosity Evolution In Electrosurgical Blade Coatings" Gregory Konesky, p. 249, Proc. of the Materials Research Society Symp., vol. 550, Boston MA, Nov. 1998.

* cited by examiner

*Primary Examiner*—Roy D. Gibson
(74) *Attorney, Agent, or Firm*—Kelly Bauersfeld Lowry & Kelley, LLP

(57) ABSTRACT

An electrosurgical knife is provided with an improved surface coating designed for substantially non-stick hemostatic cutting of soft patient tissue. The electrosurgical knife includes a conductive knife blade adapted for connection to a suitable high frequency current source for electrocauterizing tissue at the point of contact to prevent or minimize bleeding. The knife blade includes the improved surface coating formed on at least a cutting edge thereof, wherein the outer surface of the coating includes a relatively non-stick constituent such as an aromatic hydrocarbon in combination with a relatively hard constituent such as a ceramic. The surface coating is additionally loaded with a substantially uniformly dispersed matrix of conductive material for transmitting the electrical energy to patient tissue primarily by conduction.

33 Claims, 1 Drawing Sheet

ELECTROSURGICAL KNIFE

This is a continuation-in-part of U.S. Ser. No. 09/495,570, filed Feb. 1, 2000 now U.S. Pat. No. 6,409,725.

BACKGROUND OF THE INVENTION

This invention relates generally to surgical instruments, particularly with respect to improvements in devices for cutting or piercing patient tissue while minimizing or eliminating bleeding. More specifically, this invention relates to an improved surgical knife for hemostatic cutting of patient tissue, wherein the improved surgical knife has a relatively hard and long-wearing surface for contacting patient tissue substantially without sticking while providing significantly improved transfer of electrical energy for electrocauterizing patient tissue.

Electrosurgical instruments such as scalpels, knives and the like are well known in the medical arts for incising soft patient tissue with concurrent transmission of electrical energy to the contacted tissue to cauterize small blood vessels and thereby minimize bleeding. Such devices utilize a relatively high frequency electrical current passed through the typically stainless steel and conductive tool structure to disrupt blood vessels by vaporization and/or cauterization at the point of cutting contact. The electrical energy provides a source of localized heating which imparts thermal damage to contacted patient tissue and cellular layers in a manner causing denaturizaton of proteins and sealing of blood vessels. In this regard, to achieve a smooth-edged incision conducive to rapid postsurgical healing with minimal scar formation, it is highly desirable for the electrical energy to be transmitted to the contacted patient tissue in a closely controlled manner and with a substantially uniform current density in order to minimize or prevent tissue and blood vessel damage beyond the immediate area of the contacted tissue. Conversely, the absence of a closely controlled and substantially uniform current density undesirably produces uneven localized thermal tissue damage, resulting in an irregular or ragged incision margin which heals more slowly and with a higher incidence of aesthetically unappealing scar tissue. For examples of electrosurgical instruments of this general type, see U.S. Pat. Nos. 4,248,231; 4,232,676; 4,161,950; 4,033,351; 4,333,467; 4,314,559; 4,481,057; and 3,913,583.

While such electrosurgical tools have proven to be effective to control bleeding in the course of surgical procedures, problems have been encountered with respect to sticking of soft incised tissue to the surgical instrument. More particularly, charred and necrosized tissue and cells can be generated by localized excessive thermal heating, wherein such tissue and cells tend to adhere to the surgical instrument such as the cutting edge of a surgical knife. Unfortunately, the presence of such tissue and cells on the working surface of the instrument interferes with subsequent hemostatic cutting by disrupting the current field and correspondingly reduce the efficiency and efficacy of the instrument. To combat this problem during surgery, it is necessary for the surgeon to frequently replace the electrosurgical knife or the like with a clean instrument, or alternately to frequently interrupt the surgical procedure while the instrument is wiped clean with an abrasive pad or the like. In either case, the surgical procedure is prolonged and the overall risk and cost of patient care are thus increased.

In the past, significant design efforts have been directed to improvements in electrosurgical knives and the like, with a view toward providing improved transmission of electrical energy to patient tissue in a manner to reduce sticking of soft tissue to the cutting surface. In general, such design efforts have envisioned non-stick surface coatings, as described, for example, in U.S. Pat. Nos. 4,314,559; 4,333,467; 4,161,950; 4,481,057; 4,785,807; and 7,876,110. Such non-stick surface coatings have typically comprised a polymeric material such as a fluorinated hydrocarbon (e.g., polytetrafluoroethylene (PTFE, commonly known as Teflon)) for increasing the lubricity of the tool surface. These non-stick surface coatings have enabled an improvement in electrocautery knives to be obtained. Typically, however, such fluoropolymer coatings exhibit dielectric properties which may impair the efficiency and efficacy of hemostatis. In particular, U.S. Pat. Nos. 4,785,807 and 4,876,110 disclose a dual layer dielectric insulating coating designed for achieving capacitive coupling of the electrosurgical radio-frequency (RF) energy to the patient's flesh. In these two patents, at least the outer layer of the coating comprises a fluorinated hydrocarbon material having a thickness which is sufficiently thin to permit capacitive coupling of the RF electrical energy through the coating to the tissue being cut. In addition, such fluoropolymer coatings may exhibit a tendency to release from the tool substrate due to formation of microporosity, delamination and/or abrasive wear, thus exposing underlying portions of the tool substrate to direct tissue contact and related sticking problems. Such release of the coating from the tool substrate may be enhanced by the thermal heating which occurs during normal intended use.

It is believed that such non-stick polymer coatings have the potential to undergo morphological changes during use, eventually leading to delamination failure. See Konesky, "Porosity Evolution in Electrosurgical Blade Coatings", p. 249, Proc. of the Materials Research Society Symp., Vol. 550, Boston, Mass., November 1998. More specifically, such polymeric coatings are typically provided with a very thin coating thickness on the order of about 40–150 microns, wherein the coating has strong dielectric properties. A coated electrosurgical knife of this type is believed to develop a series of holes or voids of varying size and distribution in the insulative non-stick coating, wherein these holes or voids lead to nonuniform variations in the capacitive transmission of the electrical energy to the contacted patient tissue to create localized excess heating, excess tissue damage, undesired irregular sticking of tissue to the knife, and further degradation and delamination of the non-stick coating. Indeed, when microporosity extends from the outer surface of the fluorinated hydrocarbon coating to the metal tool substrate, some direct ohmic electrical energy transfer may occur, which might exacerbate the nonuniform or inhomogeneous RF electrical energy transfer to the tissue.

Additionally, the soft incised and cauterized tissue may stick to the outer surface of the electrosurgical tools with the coating as disclosed in U.S. Pat. Nos. 4,785,807 and 4,876,110. The inherent microporosity of the coating disclosed in these patents presents a higher surface energy which may promote tissue sticking.

U.S. Pat. No. 4,314,559 discloses an alternative coated electrosurgical knife having a first conductive coating applied to the knife substrate, and a second outer non-stick polymeric coating applied to fill the microscopic interstices of the first coating in an attempt to provide improved adherence of the non-stick coating to the knife. The two layer coating essentially provides a conductive underlayer with a large plurality of microscopic conductive islands exposed through gaps in the overlying non-stick outer layer. This structure inherently transmits the electrical energy to the patient tissue in a nonuniform manner with spatially varying electrical and thermal conductivity, resulting in excess heating damage of tissue and consequent tissue sticking to the knife blade. Moreover, the small pores in the outer coating are a potential source of electrical discharge arcs which can pose a serious risk of fire in a surgical operating room environment.

There exists, therefore, a need for further improvements in and to electrosurgical instruments such as an electrosurgical knife and the like, wherein the instrument is designed to transmit electrical energy to patient tissue in a closely controlled and substantially uniform manner consistent with optimized hemostatic cutting of soft tissue, substantially in the absence of sticking of such patient tissue to the instrument. Moreover, there exists a need for such electrical instruments having an improved non-stick surface coating designed for relatively long service without delamination failure. The present invention fulfills these needs and provides further related advantages.

SUMMARY OF THE INVENTION

In accordance with the invention, an improved electrosurgical instrument such as an electrosurgical knife is provided for hemostatic cutting of soft patient tissue in the course of a surgical procedure. The electrosurgical instrument comprises a conductive substrate such as a knife blade of stainless steel having an improved substantially non-stick and electrically conductive coating applied to at least the portion thereof for contacting patient tissue. The improved coating comprises a combination of conductive, non-stick and hardening agents to exhibit beneficial properties of improved coating stability, improved electrical and thermal conductivity, improved wear resistance, and a relatively low surface coefficient of friction (high lubricity).

More particularly, the improved coating comprises multiple coating layers applied to the instrument substrate in a sequence for substantially optimized adherence thereto, wherein each of the coating layers is loaded with a matrix of conductive material such as conductive particles. Alternatively, the use of a selected organic additive which can be homogeneously dissolved on a molecular scale and can pyrolize during the subsequent baking process to form a carbon residue can also be advantageously employed. The multiple coating layers include at least one base coat applied to the substrate, wherein the base coat includes the conductive material in an aqueous suspension of a hydrocarbon such as polyamide imide or polytetrafluoroethylene (PTFE) and a conductive agent. The multiple coating layers further include an outer coat loaded with the conductive material and the hardening agent, in combination with an aromatic hydrocarbon and a fluorinated hydrocarbon.

In one preferred form, the improved coating comprises a base coat, a mid coat and a top coat. The base coat preferably consists of a liquid suspension containing de-ionized water, chromic acid, and a hydrocarbon binder such as polyamide imide solution or an aqueous suspension of a fluorinated hydrocarbon such as polytetrafluoroethylene (PTFE), selected for intimate and stable bonding with the instrument substrate, wherein the suspension is loaded with conductive material such as graphite or a semi-conducting oxide particles having a particle size of about 10–20 nanometers and in a proportion of about 25–35% by weight. This base coat is applied to the substrate by spraying or dipping, allowed to dry, and then subjected to heat for a time and temperature sufficient to cure the base coat thereon.

A second or mid coat is then applied, consisting of a liquid carrier such as de-ionized water loaded with the same conductive material in a proportion of about 20–35% by weight in combination with an aqueous dispersion of a fluorinated hydrocarbon binder such as a fluorinated ethylene propylene copolymer (FEP) or perfluoroalkoxy (PFA) having a solids loading of about 20–80% by weight. This second coat is applied over the base coat by spraying or dipping, and allowed to dry.

A third or outer top coat is prepared by adding the hardening agent, for instance ceramic particles such as titania or alumina or mica in a particle size of about 10–20 nanometers, to the liquid suspension prepared in the same manner as the mid coat, with the ceramic constituent being added in a proportion of up to 30% by weight. Alternatively, an organic agent such as an acrylic polymer may be employed. This top coat is applied over the second coat by spraying or dipping, allowed to dry, and then subjected to a final heat step sufficient to produce a hard conductive composite coating on the substrate. In an alternative preferred form, this top coat may be applied to the base coat, with the mid coat being omitted.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE INVENTION

Figure 1:
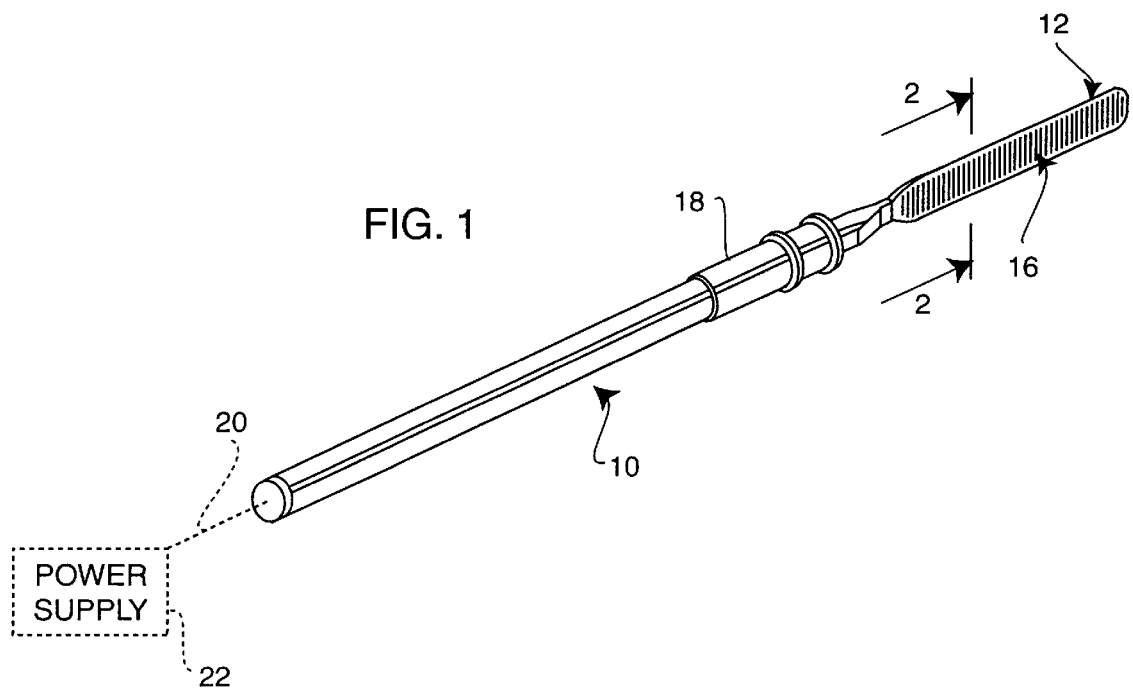
FIG. 1 is a perspective view showing an exemplary electrosurgical knife formed in accordance with the novel features of the invention.
Figure 2:
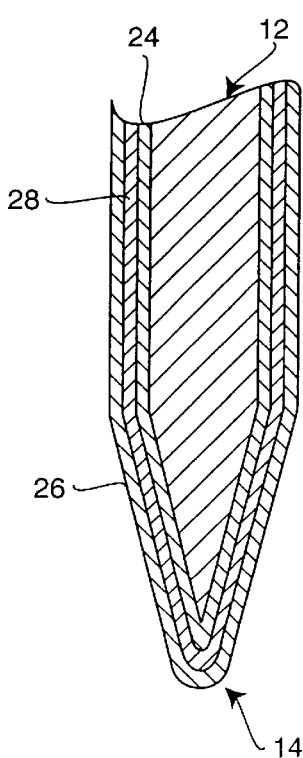
FIG. 2 is an enlarged sectional view showing the coating including base, mid and top coats according to one embodiment of the invention, taken generally on the line 2—2 of FIG. 1.

As shown in the exemplary drawings, an electrosurgical instrument in the form of an electrosurgical knife referred to generally in FIG. 1 by the reference numeral 10 is provided for hemostatic cutting of soft patient tissue in the course of a surgical procedure. The knife 10 includes a forward or distal end defining a blade 12 which is shown shaped and sharpened along at least one side edge to form a cutting edge 14 (FIG. 2). In accordance with the present invention, the knife blade 12 carries an improved surface coating referred to generally by the reference numeral 16, wherein this surface coating provides the knife 10 with beneficial properties of improved coating stability, improved electrical and thermal conductivity, improved wear resistance, and a relatively low surface coefficient of friction (high lubricity).

The illustrative electrosurgical knife 10 generally comprises the knife blade 12 protruding forwardly from a suitable sleeve-type and generally pencil shaped handle 18 adapted for manual grasping and manipulation by a surgeon in the course of applying the cutting edge 14 to incise patient tissue during a surgical procedure. The knife blade 12 is typically formed from a conductive metal such as a surgical grade stainless steel or other suitable surgical grade metal alloy or the like. A rear or proximal end of the handle 18 is coupled via one or more conductors 20 to a suitable electrical power supply 22. In use during a surgical procedure, the power supply 22 connects a relatively high frequency electrical current via the conductors 20 to the knife blade 12 for thermally cauterizing and sealing blood vessels to minimize patient bleeding. In this regard, the handle 18 is normally formed from a suitable insulative material to isolate the surgeon from the electrical signal. Throughout this application, like reference numerals will be used for like parts.

The improved electrosurgical instrument of the present invention incorporates the improved surface coating 16 on the knife blade 12 to cover at least the region thereof utilized to contact patient tissue for cutting and cauterizing. The surface coating 16 is designed for providing a low surface energy and low coefficient of friction (high lubricity) for producing smooth-edged incisions conducive to rapid healing with minimal postsurgical scarring, and with little or no sticking of residual patient tissue to the knife blade. In addition, the improved surface coating 16 exhibits relatively high electrical and thermal conductivity characteristics for transmitting the current signal to the patient tissue with a substantially uniform current density, substantially in the absence of any significant localized thermal variations along the knife blade. The improved surface coating 16 is securely bonded to the knife blade substrate for enhanced long term coating stability without delamination or peeling, and further exhibits improved surface hardness for extended wear characteristics. Importantly, although the invention is shown and described with respect to an electrosurgical knife, it will be recognized and understood that the improved surface coating 16 may be applied to other types of electrosurgical instruments such as electrosurgical needles and other electrosurgical tools which may or may not include a cutting edge.

The improved surface coating generally comprises multiple coating layers applied to the instrument substrate such as the metal knife blade 12 in a sequence for substantially optimized adherence thereto, wherein each of the coating layers is loaded with a substantially uniformly dispersed matrix of conductive material such as conductive particles or a selected organic additive having conductive properties. The multiple coating layers include at least one primer or base coat 24 (FIG. 2) applied to the substrate 12, in combination with at least one outer or top coat loaded additionally with non-stick and hardening agents for respectively providing a low surface coefficient of friction and a relatively high degree of hardness.

In one preferred form of the invention, shown in FIG. 2, coating 16 comprises base coat 24 covered by an intermediate or mid coat 28 loaded with the conductive material together with the non-stick agent. Mid coat 28 is covered, in turn, by a top coat 26, which is loaded with the conductive material, non-stick agent, and hardening agent in the form of a ceramic agent or acrylic polymer agent.

More particularly, in accordance with a preferred form of the invention, the substrate 12 such as the illustrative stainless steel knife blade having the cutting edge 14 thereon is prepared for application of the surface coating 16 by initially cleaning residual oils, grease and other contaminants from the portion thereof to be coated. Such cleaning may take place by grit blasting the substrate outer surface and/or by dipping the substrate into an acid bath, such as chromic acid. Alternately, cleaning solvents may be used, followed by washing and rinsing in de-ionized water. Substrate cleaning may also occur by baking at a relatively high temperature, such as about 400–425° C. to volatilize oils, grease and other contaminants. The optimum substrate preparation yields a clean but relatively rough etched or abraded surface for strong adherence with the base coat 24 to be applied.

The base coat 24 comprises a liquid carrier selected for relatively strong bonded adherence or attachment to the substrate 12, such as de-ionized water in solution with chromic acid and polyamide imide. This liquid carrier is loaded with the conductive material such as carbon based (e.g., graphite) or semi-conductive particles or other materials such as cobalt oxides or selected transition metal oxides, having a particle size of about 10–20 nanometers. The conductive particles are added to the liquid carrier in a proportion of about 10–50% by weight (about 14–18% by volume), and preferably about 25–35% by weight. Alternatively, the conductive material may be loaded into an aqueous suspension of a nonstick hydrocarbon, such as polytetrafluoroethylene (PTFE).

This prepared base coat 24 is applied by spraying or dipping to the selected region of the substrate 12, with a coating thickness of about 2–15 microns, and then allowed to dry. After drying, the base coat 24 is flash baked for about 2–3 minutes at a temperature of about 100–150° C. The solvents and chromic acids volatilize off during this process and leave behind the hydrocarbon with a substantially uniform dispersion of conductive particles homogeneously dispersed. The resultant baked base coat 24 is thus cured to a relatively hard state with strong mechanical adherence with the underlying substrate 12. The cured base coat 24 has a coating thickness within a range of about 2–10 microns, and preferably about 7.5–10 microns.

After the base coat 24 has cooled substantially to ambient temperature, the intermediate or mid coat 28 is applied thereto. The mid coat also comprises a liquid carrier loaded with the conductive material and additionally loaded with the non-stick agent. In one form, the liquid carrier comprises an aqueous media such as de-ionized water loaded with the conductive particles (as previously described) and the non-stick agent in the form of a polymeric binder such as an aqueous suspension of an aromatic hydrocarbon such as fluorinated ethylene propylene copolymer (FEP) or perfluoroalkoxy (PFA) having a solids loading of about 20–60% by weight. The conductive and non-stick agents are substantially uniformly dispersed within the liquid carrier in a proportion of about 38–44% by weight and preferably about 25–30% by weight conductive particles. A binder such as oleic acid may be added to the mixture in a minor amount to stabilize the suspension. A surfactant such as Triton ×100 available from Rohm & Haas Co. of Montgomeryville, Pa., may also be added to enhance rheological characteristics of the mixture. When such binder and/or surfactant are used, such agents are added in a combined amount of about 1–2% by weight. The combined solids loading represented by the conductive particles and the non-stick agent is about 38–44% by weight (about 20–26% by volume). Alternative liquid carriers may be used, such as organic based liquids including, for example, alcohols, ketones, aliphatic or aromatic compounds, and mixtures thereof.

The prepared mixture comprising the mid coat 28 is applied to the substrate 12 over the base coat 24 by spraying or dipping to flow into the interstices of the base coat for intimate contact and adhesion therewith. The mid coat 28 is applied with a coating thickness of about 25–50 microns, and is allowed to dry.

The top or outer coat 26 is then prepared and applied to the substrate 12, to cover the mid coat 28 after suitable cooling thereof substantially to ambient temperature. The top coat 26 comprises, in the preferred form, the same suspension mixture as described above for the mid coat 28 with the addition of a hardening agent, for instance a ceramic agent in the form of titania or alumina or mica having a particle size of about 10–20 nanometers. The selected ceramic agent is added in a proportion of about 20–30% by weight, and preferably about 25% by weight. The total solids loading of the top coat 26 is about 38–44% by weight, and preferably about 38–40% by weight, wherein the relative proportions of the solids to each other is about 30–67% and preferably about 30–33% by weight conductive particles, about 30–67% and preferably about 45–50% by weight non-stick agent, and about 20–35% and preferably about 25% by weight ceramic agent. A substantially homogeneous suspension is created with substantially uniformly dispersed solids by milling at a low speed in a Nalgene jar containing ceramic grinding media for about 4–18 hours.

The thus-prepared top coat 26 is then applied by spraying or dipping to cover the mid coat 28, with intimate flow into the interstices of the mid coat 28 for substantially optimized adhesion thereto, with a coating thickness of about 25–30 microns. After drying in air, the mid and top coats 28, 26 are subjected to a baking and curing step at a relatively high temperature of about 400–415° C. for a period of up to about 15 minutes. This final higher bake temperature for the mid and top coats 28, 26 beneficially enables the non-stick and ceramic agents to melt-flow adhere respectively with the underlying coat. In the cured state, the mid and top coats 28, 26 have a combined thickness of about 20–40 microns and preferably about 20–30 microns. The combined thickness of the base, mid and top coats 24, 28 and 26 is about 30–50 microns and preferably about 35 microns.

During the baking process, the fluorinated hydrocarbon component sinters together to form a network of fluorinated hydrocarbon particles bonded together. The aromatic hydrocarbon components of the coating exhibit melt-flow characteristics, which cause the interstices between the fluorinated hydrocarbon particles to be substantially filled and sealed. Moreover, the outer surface of the final coating essentially comprises the aromatic hydrocarbon such as FEP of PFA, with the conductive and ceramic materials intimately and substantially homogeneously dispersed therein.

Figure 3:
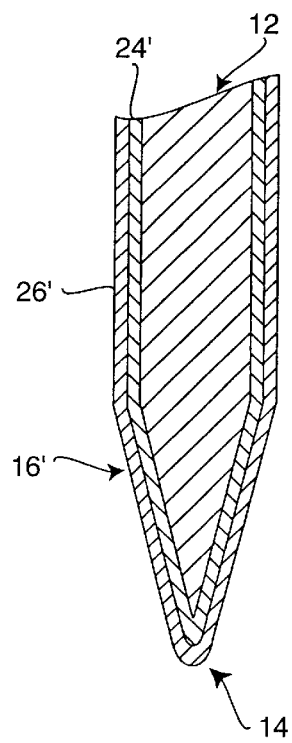
FIG. 3 is an enlarged sectional view similar to FIG. 2, but illustrating base and top coats according to another embodiment of the invention.

In another preferred form of the invention, shown in FIG. 3, coating 16' includes a base coat 24' and a top coat 26'. The base coat 24' is covered by a top coat 26', which is loaded with the conductive material together with the non-stick agent, and hardening agent.

More particularly, the substrate 12, such as the illustrative stainless steel knife blade having the cutting edge 14 thereon, is prepared for application in a manner substantially similar to that described above in reference to FIG. 2. Such cleaning may take place by grit blasting the substrate outer surface and/or by dipping the substrate into an acid bath, such as chromic acid. Alternately, cleaning solvents may be used, followed by washing and rinsing in de-ionized water. Substrate cleaning may also occur by baking at a relatively high temperature, such as about 400–425° C. to volatilize oils, grease and other contaminants. The optimum substrate preparation yields a clean but relatively rough etched or abraded surface for strong adherence with the base coat 24' to be applied.

The base coat 24' preferably has the same composition as that described in reference to base coat 24 shown and described in reference to FIG. 2, and is applied to substrate 12 and cured in a substantially identical manner. After the base coat 24' has cooled substantially to ambient temperature, top coat 26' is applied thereto. The top coat comprises a liquid carrier loaded with the conductive material, a non-stick agent and a hardening agent. In one form, the liquid carrier comprises an aqueous media such as de-ionized water loaded with the conductive particles (as previously described) and the non-stick agent in the form of a polymeric binder such as an aqueous suspension of an aromatic hydrocarbon such as fluorinated ethylene propylene copolymer (FEP) or perfluoroalkoxy (PFA) having a solids loading of about 20–60% by weight. In one form, the hardening agent preferably comprises a ceramic agent in the form of alumina or mica having a particle size of about 10–20 nanometers. It will be understood, however, that alternative hardening agents such as an acrylic polymer or the like may be sued. In the caes of a ceramic hardening agent, the selected ceramic agent is added in a proportion of about 20–35% by weight, and preferably about 25% by weight. The total solids loading of the top coat 26' is about 38–44% by weight, and preferably about 38–40% by weight, wherein the relative proportions of the solids to each other is about 30–67% and preferably about 30–33% by weight conductive particles, about 30–67% and preferably about 45–50% by weight non-stick agent, and about 20–35% and preferably about 25% by weight ceramic agent.

A substantially homogeneous suspension is created with substantially uniformly dispersed solids by milling at a low speed in a Nalgene jar containing ceramic grinding media for about 4–18 hours. The conductive, non-stick and ceramic agents are substantially uniformly dispersed within the liquid carrier. A binder such as oleic acid may be added to the mixture in a minor amount to stabilize the suspension. A surfactant such as Triton x100 available from Rohm & Haas Co. of Montgomeryville, Pa., may also be added to enhance rheological characteristics of the mixture. When such binder and/or surfactant are used, such agents are added in a combined amount of about 1–2% by weight. The combined solids loading represented by the conductive particles and the non-stick agent is about 38–44% by weight (about 20–26% by volume). Alternative liquid carriers may be used, such as organic based liquids including, for example, alcohols, ketones, aliphatic or aromatic compounds, and mixtures thereof.

The prepared mixture comprising the top coat 26' is applied to the substrate 12 over the base coat 24' by spraying or dipping to flow into the interstices of the base coat for intimate contact and adhesion therewith, with a coating thickness of about 25–30 microns. After drying in air, the top coat 26' is subjected to a baking and curing step at a relatively high temperature of about 400–415° C. for a period of up to about 15 minutes. This final higher bake temperature for the top coat 26' beneficially enables the non-stick and ceramic agents to melt-flow adhere respectively with the underlying base coat. In the cured state, the top coat 26' has a thickness of about 20–40 microns and preferably about 20–30 microns. The combined thickness of the base and top coats 24' and 26' is about 30–50 microns and preferably about 35 microns.

In a further alternative preferred embodiment of the invention, the stainless steel substrate blade 12 is initially degreased and then sandblasted to prepare the appropriate surface thereof for subsequent application of surface coatings. At the conclusion of the sandblasting step, the blade 12 is desirably subjected to a stream of pressurized air to blow off and remove any residual particulate. The thus-cleaned substrate blade is then coated with an initial primer or base coat 24' (FIG. 3) with an electroconductive primer coating such as "Teflon" Primer—Black, Product No. 855-023, marketed by E. L. DuPont de Nemours & Co. (DuPont) of Wilmington, Del. This base coat 24' comprises a liquid suspension including conductive carbon particulate in the form of carbon black, fluorinated ethylene polypropylene ("FEP"), polytetrafluoroethylene ("PTFE"), a hardening agent such as mica and/or titanium dioxide, polyimide-imide, triethylamine, furfuryl alcohol, methyl pyrrolidone and water. The base coat 24' is applied to the substrate 12 by spraying or dipping, and is then allowed to dry. After drying, the base coat 24' may be subjected to heat for a time and temperature sufficient to cure the base coat on the substrate. The resultant baked base coat 24' is thus cured to a relatively hard state, and then allowed to cool to ambient temperature.

Once the base coat 24' is cured and cooled, a top coat 26' (FIG. 3) is applied over at least a portion of and preferably to substantially cover the base coat 24'. This top coat 26' also comprises an electroconductive coating material such as "Teflon" Topcoat Finish—Black, Product No. 855-101, also marketed by DuPont. This top coat comprises a liquid suspension including conductive carbon particulate in the form of carbon black, perfluoroalkoxy resin ("PFA"), PTFE, a hardening agent such as an acrylic polymer, triethanolamine, an aromatic hydrocarbon, trimethyl benzene, diethylene glycol monobutyl ether, oleic acid, octylphenoxypolyethoxyethanol surfactant and water. The top coat 26' is applied over the base coat 24' by spraying or dipping, and is then allowed to dry. After drying, the top coat is subjected to a heat step sufficient to produce a hard conductive composite coating on the exterior of the substrate. The dried coatings on the substrate are then subjected to a baking and final curing step at a relatively high temperature, such as on the order of about 800° F. for about 5 minutes. This final higher temperature bake step enables the non-stick and hardening agents to melt-flow together and adhere to the underlying surfaces. The combined thickness of the base and top coats 24', 26' in this embodiment is about 1 mil.

Both of the resultant multi-layer surface coatings 16 and 16', as applied to the substrate knife blade 12 in accordance with the various above described embodiments of the invention, exhibit a combination of beneficial properties which provide superior hemostatic cutting in the course of a surgical procedure. More particularly, surface coatings 16 and 16' combine enhanced electrical and thermal conductivity attributable to the conductive particles, with low surface energy accompanied by strong adherence of the fluoropolymer non-stick agent relative to the underlying substrate. With the addition of the hardening agent in the outer top coats 26 and 26', the exterior of surface coatings 16 and 16' are hard and stable to provide long wear characteristics without development of delamination, peeling, or the formation of pores and voids which would otherwise disrupt the desired substantially uniform coupling of current and related thermal energy to patient tissue. By providing substantially homogeneous conductive electrical coupling between the knife blade and patient tissue, localized arcing and related excessive tissue damage and/or risk of fire are substantially minimized. Additionally, the multi-layer structure of the three-coat surface coating 16 also provides a greater cross section for thermal conductivity, thereby increasing the tendency to maintain uniform temperature properties across the surface area.

During the baking process, the fluorinated hydrocarbon component sinters together to form a network of fluorinated hydrocarbon particles bonded together. The aromatic hydrocarbon components of the coating exhibit melt-flow characteristics, which cause the interstices between the fluorinated hydrocarbon particles to be substantially filled and sealed. Moreover, the outer surface of the final coating essentially comprises the aromatic hydrocarbon such as FEP of PFA, with the conductive and hardening materials intimately and substantially homogeneously dispersed therein.

A variety of modifications and improvements in and to the improved electrosurgical instrument of the present invention, and its related method of production, will be apparent to persons skilled in the art. Accordingly, no limitation on the invention is intended by way of the foregoing description and accompanying drawings, except as set forth in the appended claims.

What is claimed is:

1. An electrosurgical instrument for cooperation with an electrical power supply, said electrosurgical instrument of the type including a handle, one or more conductors coupling the power supply to the handle, and a knife blade for use in the hemostatic cutting of soft tissue, said cutting being accomplished through the transfer of electrical energy from the knife blade to a patient during surgery primarily through conduction, said knife blade comprising:
   a conductive substrate having a surface; and
   a top coat applied to at least a portion of the conductive substrate;
   said top coat including a non-stick agent and a hardening agent substantially uniformly impregnated with a conductive agent.

2. The electrosurgical instrument according to claim 1 wherein at least a portion of the surface of said conductive substrate is coated with a base coat loaded with said conductive agent, and wherein said top coat is applied to cover at least a portion of said base coat.

3. The electrosurgical instrument of claim 2 wherein said top coat is applied to substantially cover said base coat.

4. The electrosurgical instrument of claim 3 wherein said top coat comprises DuPont 855-101.

5. The electrosurgical instrument of claim 4 wherein said base coat comprises DuPont 855-023.

6. The electrosurgical instrument according to claim 1 wherein at least a portion of the surface of said conductive substrate is coated with a base coat loaded with said conductive agent, wherein at least a portion of said base coat is coated with a mid coat loaded with said conductive agent and said non-stick agent, and wherein said top coat is applied to cover at least a portion of said mid coat.

7. The electrosurgical instrument of claim 1 wherein the conductive substrate comprises an electrosurgical knife blade.

8. The electrosurgical instrument of claim 1 wherein said conductive agent comprises conductive material selected from the group consisting of carbon and semiconductive metal oxides.

9. The electrosurgical instrument of claim 1 wherein said non-stick agent comprises an aromatic hydrocarbon binder.

10. The electrosurgical instrument of claim 9 wherein said aromatic hydrocarbon binder is selected from the group consisting of fluorinated ethylene propylene copolymer (FEP) and perfluoroalkoxy (PFA).

11. The electrosurgical instrument of claim 1 wherein said non-stick agent comprises a fluorinated hydrocarbon.

12. The electrosurgical instrument of claim 11 wherein said fluorinated hydrocarbon comprises polytetrafluoroethylene.

13. The electrosurgical instrument of claim 1 wherein said hardening agent is selected from the group consisting of ceramic and polymeric agents.

14. The electrosurgical instrument of claim 1 wherein said hardening agent is selected from the group consisting of titania, alumina, mica, and acrylic based polymers.

15. A method of making an electrosurgical instrument for use in cooperation with an electrical power supply, said electrosurgical instrument of the type including a handle, one or more conductors coupling the power supply to the handle, and a knife blade having a conductive substrate, for use in the hemostatic cutting of soft tissue, said cutting being accomplished through the transfer of electrical energy from the knife blade to a patient during electrosurgical surgery primarily through conduction, said method comprising the steps of:

applying a top coat to at least a portion of the conductive substrate, wherein the top coat includes a non-stick agent and a hardening agent substantially uniformly impregnated with a conductive agent.

16. The method of claim 15 further includes the step of applying a base coat loaded with said conductive agent to at least a portion of the substrate before the step of applying the top coat to cover at least a portion of the base coat.

17. The method of claim 15 further including the steps of applying a base coat loaded with said conductive agent to at least a portion of the substrate, and thereafter applying a mid coat loaded with said conductive agent and said non-stick agent to cover at least a portion of said base coat before applying the top coat to cover at least a portion of the mid coat.

18. The method of claim 15 further including the step of cleaning at least a portion of the substrate in preparation for said step of applying said top coat.

19. The method of claim 15 wherein said step of applying said top coat includes subjecting the top coat to heat for a sufficient time to cure.

20. The method of claim 15 wherein the conductive agent comprises conductive material selected from the group consisting of carbon and semiconductive metal oxides.

21. The method of claim 15 wherein the hardening agent is selected from the group consisting of ceramic and polymeric agents.

22. The method of claim 15 wherein the hardening agent is selected from the group consisting of titania, alumina, mica, and acrylic based polymers.

23. The method of claim 16 wherein the combined thickness of the base and top coats is about 30–50 microns.

24. The method of claim 16 wherein said step of applying said top coat to cover at least a portion of said base coat comprises applying said top coat to substantially cover said base coat.

25. The method of claim 24 wherein said top coat comprises DuPont 855-101.

26. The method of claim 25 wherein said base coat comprises DuPont 855-023.

27. An electrosurgical instrument, comprising:
a conductive substrate; and
a surface coating applied to at least a portion of said substrate, said surface coating including a conductive agent, a non-stick agent and a hardening agent selected from the group consisting of ceramic and polymeric agents.

28. The electrosurgical instrument of claim 27 wherein said hardening agent is selected from the group consisting of titania, alumina, mica, and acrylic based polymers.

29. The electrosurgical instrument of claim 27 further including a base coat loaded with said conductive agent and applied to cover at least a portion of said substrate, said surface coating comprising a top coat applied to cover at least a portion of said base coat.

30. The electrosurgical instrument of claim 29 wherein said base coat comprises DuPont 855-023.

31. The electrosurgical instrument of claim 30 wherein said top coat comprises DuPont 855-101.

32. The electrosurgical instrument of claim 29 wherein said top coat comprises DuPont 855-101.

33. The electrosurgical instrument of claim 27 further including a base coat loaded with said conductive agent and applied to cover at least a portion of said substrate, a mid coat loaded with said conductive agent and said non-stick agent and applied to cover at least a portion of said base coat, said surface coating comprising a top coat applied to cover at least a portion of said mid coat.

* * * * *